United States Patent [19]

Nakajima

[11] Patent Number: 4,800,869
[45] Date of Patent: Jan. 31, 1989

[54] ENDOSCOPE

[75] Inventor: Shigeru Nakajima, Tokyo, Japan

[73] Assignee: Olympus Optical Co. Ltd., Tokyo, Japan

[21] Appl. No.: 153,334

[22] Filed: Feb. 8, 1988

[30] Foreign Application Priority Data

Feb. 13, 1987 [JP] Japan ................................. 62-30759
Apr. 6, 1987 [JP] Japan ................................. 62-84409
Dec. 17, 1987 [JP] Japan ................................. 62-31937

[51] Int. Cl.⁴ .............................................. A61B 1/12
[52] U.S. Cl. ...................................................... 128/4
[58] Field of Search ........................................ 128/4, 6

[56] References Cited

U.S. PATENT DOCUMENTS

| 4,261,343 | 4/1981 | Ouchi et al. | 128/4 |
| 4,325,362 | 6/1983 | Ouchi et al. | 128/4 |
| 4,402,310 | 9/1983 | Kimura | 128/4 |
| 4,548,197 | 10/1985 | Kinoshita | 128/4 |
| 4,748,970 | 6/1988 | Nakajima | 128/4 |

Primary Examiner—William H. Grieb
Attorney, Agent, or Firm—Ladas & Parry

[57] ABSTRACT

An endoscope comprising an elongated insertion section inserted into the cavity of a human body, an operating section connection to an end of the inserted section and controlling the inserted section from outside the human body, and a universal code extending from the operating section. The universal code has a connector arranged at that end thereof which is opposite to the operating section, and connected to water, air and gas sources. Liquid tubes extend through the inserted and operating sections and universal code to enable the gas, air and water sources to communicate with the outside through the foremost end of the inserted section. A switch valve is arranged within these liquid tubes, dividing them into upper and lower side tubes. The switch valve is attached to the operating section to selectively communicate with or shut off the upper and lower side tubes. When they are shut off, air which has leaked from the gas source can be released through a leak passage to the outside and the outlet opening of this leak passage can selectively be closed by hand.

20 Claims, 17 Drawing Sheets

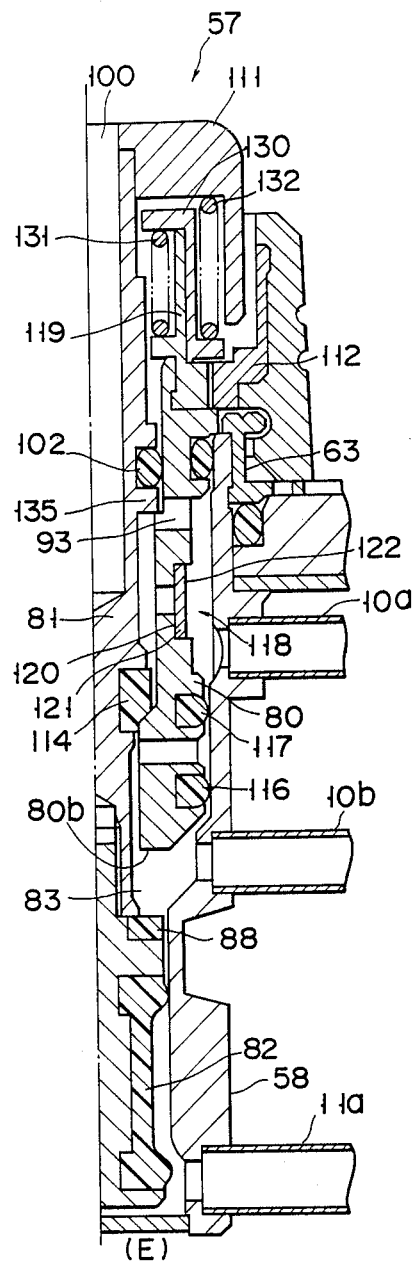
F I G. 9

ENDOSCOPE

BACKGROUND OF THE INVENTION

1. Field of the Invention

The present invention relates to an endoscope provided with a switch valve for enabling air, gas and water to be selectively supplied.

2. Description of the related art including information disclosed under §§1.97-1.99

Generally, there is the possibility that inflammable gas remains in the cavity, particularly in the lower digestive organs such as the intestines of a human body. When the high frequency treatment is applied, using the endoscope, to the cavity of the human body in which this inflammable gas remains, therefore, there is the danger that the inflammable gas is burst up by high frequency energy caused by the treatment. In order to prevent this, noninflammable gas such as carbon dioxide is supplied into the cavity through the endoscope to replace the inflammable gas before the high frequency treatment is applied.

Endoscopes which have a unit for supplying a noninflammable gas into a body cavity, as well as an air/water supply unit, is disclosed in Japanese Utility Model Disclosures No. 60-32902 and No. 61-29704. The gas-supplying unit comprises a gas supply pipe and a gas control valve. The endoscope has an air/water supply button and a gas supply button. The air/water supply button is depressed to supply either air or water through an air/water supply pipe into a body cavity. The gas supply button is depressed to supply the noninflammable gas into a body cavity. These buttons are arranged side by side. Provided with two supply units, the endoscope is relatively large. Further, since the endoscope has two buttons which must be selected and depressed, the operation efficiency of the endoscope is rather low.

In most cases, once the air/water supply unit or the gas supply unit has been operated, thus supplying air or water, or alternatively a non-inflammable gas, into a body cavity, the other supply unit need not be operated. In view this fact, it would suffice to use only one supply unit to supply air or water, or the non-inflammable gas into a body cavity.

Japanese Utility Model Disclosure No. 57-103621, discloses an endoscope wherein two kinds of valve assemblies, one for switching air and water and the other for switching gas and water, can be incorporated into a valve seat at the operating section thereof. The endoscope of this type can be small-sized and its operation is easy because it has no independent gas supply line.

In the case of the gas and water switching valve assembly, however, the gas passage is sealed at the upper and lower sides thereof by seal rings which are made of resilient material and which are pressed against the metal wall of the passage due to their resiliency. Their sealing capacity is thus limited. Further, there is the danger that gas pressurized so high as to overcome their sealing capacity may be supplied because the gas bomb in which the highly-pressurized gas is contained and which is connected directly to the endoscope is used as the gas source. This is caused in a case where the user makes a mistake in adjusting the supply pressure of gas at the outlet of the gas bomb because the endoscope is not provided with a relief valve. When the gas pressurized so high as to overcome the sealing capacity of the seal rings is supplied into the cavity of a patient, he will be damaged heavily. Furthermore, there is also the danger that gas not high in pressure but unnecessarily large in amount may be supplied to the patient when the seal members exchanged in the valve assembly have already something of flaws.

SUMMARY OF THE INVENTION

The present invention is intended to eliminate the above-mentioned drawbacks of the conventional endoscope.

The object of the present invention is therefore to provide an extremely safe endoscope, compact in construction, easy to operate and capable of eliminating the danger that gas so high in pressure or so large in amount as mentioned above may be supplied to the patient.

This object of the present invention can be achieved by an endoscope including an insertion section inserted into the cavity of a human body and provided with a nozzle at one end thereof on the cavity side through which liquid is jetted, an operating section connected to the other end of said insertion section and capable of controlling said insertion section from outside the cavity, and a universal code which is connected to said operating section at one end thereof, said endoscope further comprising a fluid source; a connector connected to the universal code on a side opposite to the operating section and capable of being connected to the fluid source; a fluid supply tube means extended in said insertion section and operating section and also in said universal code, said means being communicated with the nozzle in said insertion section and also communicated with said fluid source through said connector; and a switch valve means located on the way of said fluid supply tube means to branch this fluid supply tube means to upper and lower side tube means, wherein said switch valve means comprises a valve seat arranged at said operating section and communicated with an inner hole which has an outlet port connected with said upper side tube means and an inlet port connected with said lower side tube means, and a valve assembly inserted into said inner hole and shifted between a first position where said inlet and outlet ports are shielded and a second position where the inlet and outlet ports are communicated with each other and wherein said valve assembly has a leak passage, which can be selecting closed, for enabling fluid leaked through the inlet port to be released outside through an outlet opening when it is at said first position.

According to the endoscope of the present invention, gas leaked can be introduced outside through the leak passage communicated with a gas outlet tube of the valve assembly to keep the patient safe, even when the pressure of a gas supply source is mistakenly set higher than needed and so high as to overcome the sealing capacity of the seal rings or even when the seal members are damaged.

BRIEF DESCRIPTION OF THE DRAWINGS

FIG. 9 is a view similar to FIG. 7, showing a second variation of the gas and water switching valve.

DETAILED DESCRIPTION OF THE PREFERRED EMBODIMENTS

Figure 1:
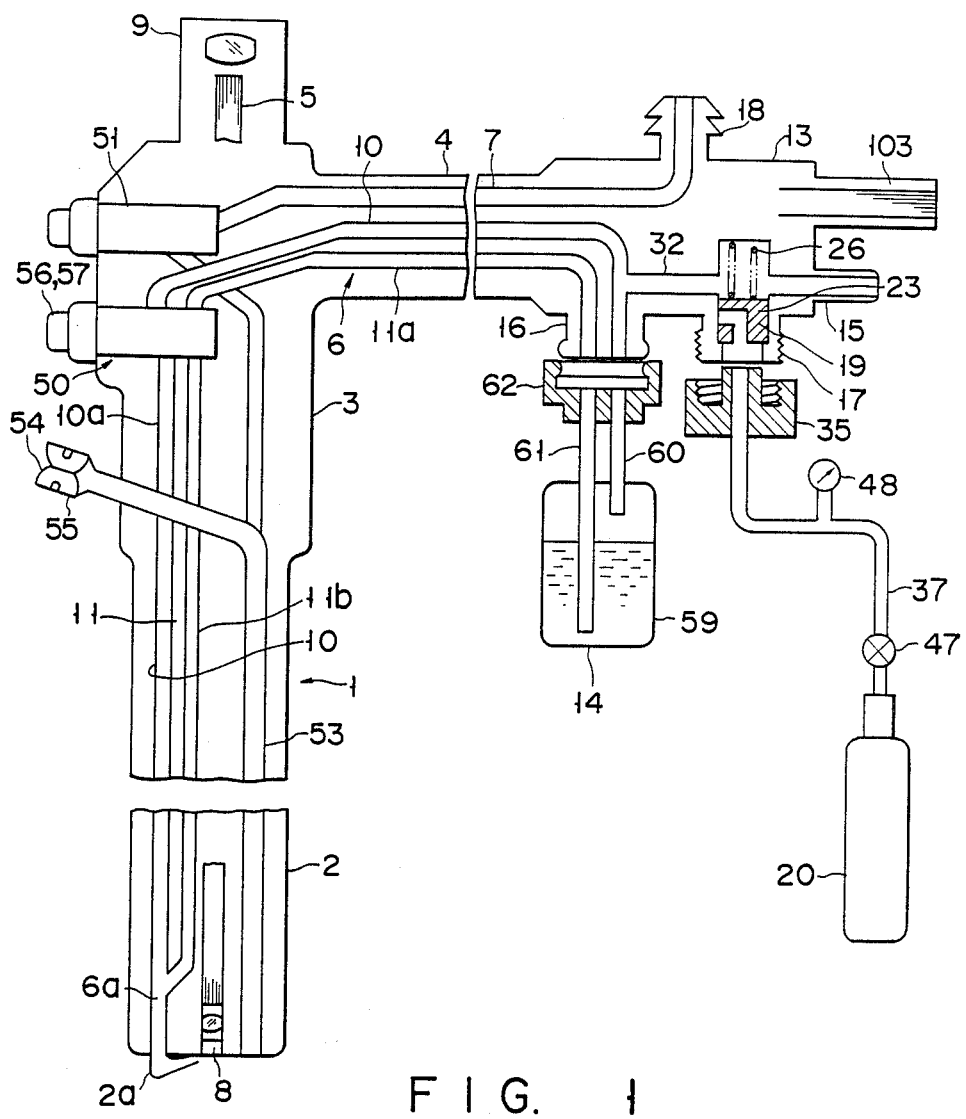
FIG. 1 shows a first example of the endoscope according to the present invention.

FIGS. 1 through 5 show a first example of the endoscope according to the present invention.

Endoscope body 1 has elongated insertion section 2 inserted into the cavity of a human body, section 3 connected to the base end of insertion section 2 and serving to operate insertion section 2 from outside, and universal code 4 extending from operating section 3. Arranged at that foremost end of insertion section 2 which is opposite to operating section 3 are an illumination window (not shown) through which light fed from light guide fiber bundle 103 is emitted to the cavity wall, observation window 8 for receiving light reflected from the cavity wall, and nozzle 12 directed toward observation window 8 to blow water or air against observation window 8. Eyepiece 9 through which the operator observes the cavity wall is also arranged at that back end of operating section 3 which is opposite to insertion section 2. Observation window 8 and eyepiece 9 are optically connected each other by image guide fiber bundle 5 which is extended through insertion and operating sections 2 and 3.

Liquid supply means 6 and suction tube 7 are extended through insertion and operating sections 2 and 3 and universal code 4.

Liquid supply means 6 has air and water supply tubes 10 and 11, and water supply tube 11 consists of upstream and downstream side tubes 11a and 11b. Air and water supply tubes 10 and 11 are united at a position adjacent to the foremost end of insertion section 2 to form liquid supply tube 6a, which is connected to nozzle 2a at the foremost end of inserted section 2. Liquid supply means 6 and suction tube 7 extend, passing through universal code 4, to connector 13 arranged at that end of universal code 4 which is opposite to operating section 3. Connector 13 can be connected to a light source means (not shown) and water tank 14 which will be described later, and liquid supply means 6 can receive air from an air pump in the light source means and water from water tank 14.

Connector 13 has air supply base 13 projected, like something of a fine tube, from that end face of universal code 4 which is opposite to the operating section 3, and connected to the air pump in the light source means, water and gas supply bases 16 and 17 each projected from the side of universal code 4, and suction base 18 which can be connected to a suction pump (not shown). Water supply base 16 is of the double cylinder type, having a center passage through which water can be passed, and a ring-shaped passage through which air can be passed and which is formed around the outer circumference of the center passage. The center passage is communicated with water supply tube 11 while the ring-shaped passage with air supply tube.

Switch valve 19 is housed in gas supply base 17 of connector 13. Switch valve 19 communicates air supply tube 10 with gas supply base 17 but shuts it off from air supply base 15 when gas bomb which is filled with a noninflammable gas such as carbon dioxide is connected to gas supply base 17, while switch valve 19 communicates air supply tube 10 with air supply base 15 but shuts it off from gas supply base 17.

Figure 2:
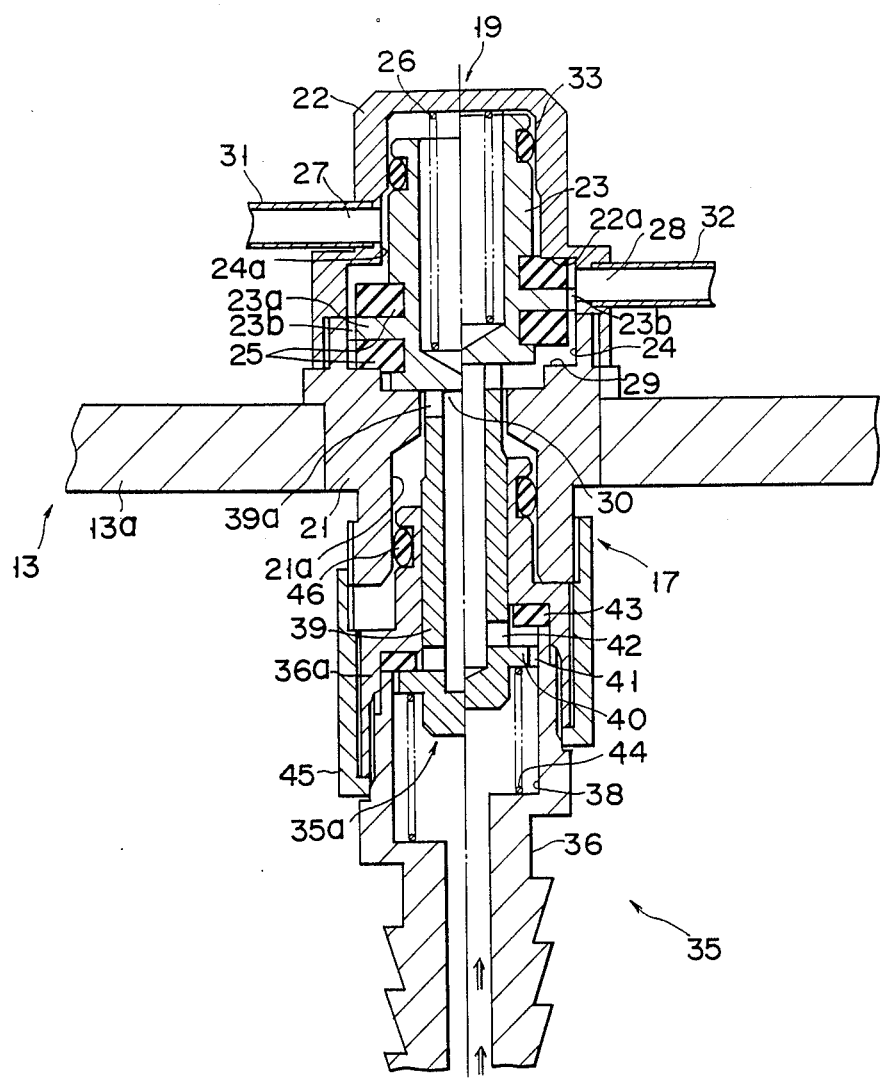
FIG. 2 is a sectional view showing a gas supply base of the endoscope for receiving noninflammable gas and a switch valve housed in the gas supply base wherein the gas supply base is not connected to a gas connector at the left of a dot and dash center line in FIG. 2 but connected thereto at the right of the line.

As shown in FIG. 2, gas supply base 17 is provided with cylindrical base member 21 attached to outer wall 13a of the connector, and this base member has inner hole 21a and gas port 30 which is coaxial to inner hole 21a. Switch valve 19 is arranged on the inner end of base member 21 in connector 13 and it includes cup-like housing 22 attached to the inner end of base member 21, and piston 23 movable in this housing along the axial line thereof. Piston 23 is made hollow and coil spring 26 which urges the piston toward base member 21 is housed in this hollow portion. Attached round the upper and outer circumference of piston 23 is seal ring 33 which is engaged with the inner face of a small-diameter portion of housing 22 (or an upper portion of housing 22 in FIG. 2). The hollow portion in piston 23 is so closely sealed by seal ring 33 as to prevent dust and the like from entering into it. Air is thus prevented from staying in the air passage, so that the air passage can be cleaned by the passing air.

Housing 22 is formed as a stepped cylinder. A large-diameter portion in the housing which is located adjacent to the base member is combined with base member 21 to form between piston 23 and the large-diameter portion a ring-shaped valve chamber 24 which is communicated with gas inlet port 30 in the base member, and another portion in the housing which extends between the small- and large-diameter portions is combined with piston 23 to form ring-shaped groove 24a between them. Further, housing 22 is provided with air inlet port 27 which is communicated with ring-shaped groove 24a, and air outlet port 28 which is communicated with valve chamber 24. Air inlet port 27 is communicated with air supply base 15 (FIG. 1) through tube 31, while air outlet port 28 with air supply tube 10 through tube 32.

Flange 23a is projected outward and in the radial direction from piston 23 in chamber 24. The outer circumferential face of this flange is provided with plural grooves extending along the axial direction to enable port 28 to be communicated with port 30, and it serves to guide piston 23 relative to the inner wall of valve chamber 24. Valve members 25 and 25 are arranged on both ring-shaped faces of flange 23a and pressed against valve seat 29 of base member 21 or valve seat 22a of housing 22, thereby enabling valve chamber 24 to be shielded from gas inlet port 30 or air inlet port 27. Since piston 23 is usually urged toward base member 21 by spring 26, ports 27 and 28 are communicated with each other but port 30 is shielded.

Gas connector 35 which is communicated with gas bomb 20 through gas connecting hose 37 can be connected to that outer end of base member 21 which is opposite to housing 22. Connector 35 includes stop valve 35a which allows gas to flow when connector 35 is connected to base member 21 but which stops gas when connector 35 is released from base member 21.

Connector 35 has hollow connector body 36 provided with a small-diameter portion which can be connected to gas bomb through gas supply hose 37 (FIG. 1), and a large-diameter portion which forms valve chamber 38. Screwed onto the outer circumference of the large-diameter portion of this connector body is the large-diameter base end of stepped hollow connecting member 36a whose small-diameter foremost end can be fitted into inner hole 21a of the base member. Piston 39 which has such an outer diameter as enables it to be inserted into port 30 of the base member at the foremost end portion thereof and which has flange 40 projected outward in the radial direction thereof is housed, slidable in the axial direction, in valve chamber 38 of the connector body and the hollow portion of the connecting member. Further, ring 45 which can connect the connector body to base member 21 is held, rotatable round the axial line thereof, by connecting member 36a and connector body 36. Valve seat member 43 made of resilient material and combined with flange 40 of the piston to form a stop valve is arranged between the stepped portion of the inner hole of connecting member 36a and connector body 36, and flange 40 of the piston is usually urged against this valve seat member by spring 44. The urging force of coil spring 44 is set larger than that of coil spring 26 of switch valve 19.

Piston 39 has plural bores 41 formed on the outer circumference of flange 40 with a certain interval interposed between the adjacent bores and extending in the axial direction thereof, and these bores 41 are closed when flange 40 is contacted with valve seat member 43. Further, piston 39 has plural bores 42 radially directed in that circumferential wall thereof which is adjacent to flange 40, and formed with a certain interval interposed between the adjacent bores. Piston 39 also has bore 39a radially directed in that circumferential wall thereof which is opposite to flange 40. These radially-directed bores 42 and 39a are communicated with each other through the inner hole of connecting member 39.

When gas connector 35 is to be connected to gas supply base 17, the foremost ends of piston 39 and connecting member 36a are inserted into port 30 and inner hole 21a of the base member, respectively. Ring 45 is then screwed onto the outer circumference of the base member. Gas supply base 17 is thus held under such a condition as shown right the center line in FIG. 2.

More specifically, coil spring 44 of gas connector 35 is set to have an urging force larger than that of coil spring 26 of switch valve 19. Piston 23 is thus pushed by piston 39 and struck against the ceiling of housing 22, so that one valve member 25 can be separated from valve seat 29 and that other valve member 25 on the opposite side can be contacted with valve seat 22a. Therefore, port 27 is shut off from ports 28 and 30 but ports 28 and 30 are communicated with each other through grooves 23b.

Piston 39 of the gas connector is moved against spring 44 by piston 23 which is struck against the ceiling of housing 22. Valve member 40 is thus separated from valve seat 43 and valve chamber 38 is communicated with port 28 through bores 41, 42, 39a and valve chamber 24. Sealing between connector 35 and base member 21 is attained by seal member 46 in this case to prevent leakage. When switch valve 47 of gas bomb 20 shown in FIG. 1 is then opened, gas can be supplied to air supply tube 10 through port 28 and tube 32. Numeral 48 in FIG. 1 denotes a pressure gage.

When gas connector 35 is not connected to gas supply base 17, therefore, air can be fed through tube 10 and when gas connector 35 is connected to gas supply base 17, port 28 is automatically communicated with port 30 to supply gas through tube 10.

As shown in FIG. 1, air and water switching valve 50 and suction switching valve 51 are arranged adjacent to each other at operating section 3. Air and water switching valve 50 is located in air and water supply tubes 10 and 11 to selectively supply either air or water to liquid supply tube 6a. Suction switching valve 51 is located in suction tube 7. Suction tube 7 is communicated with channel 53 which is extended through insertion section 2 and through which treating tools are inserted. Suction in the cavity of the human body can be made through the treating tools inserting channel and suction tube. An end of channel 53 through which treating tools are inserted is opened outside operating section 3 and plug 55 is detachably attached to this opening of channel 53.

As will be described in detail later, two kinds of exchangeable valve assemblies including first air and water switching valve assembly 56 and second gas and water switching valve assembly 57 can be used as air and water switching valve 50. When air and water are to be switched, first valve assembly 56 is attached to valve seat 58 of air and water switching valve 50, air supply base 15 is connected to an air supply pump (not shown) in the light source means, and nothing is connected to gas supply base 17. When gas and water are to be switched, second valve assembly 57 is attached instead of first valve assembly 56 and gas connector 35 shown in FIG. 2 is connected to gas supply base 17. It is needed in any case that each of circuits necessary to supply air, water and gas is completed by connecting water supply tank 14 to water supply base 16.

As shown in FIG. 1, water supply tank 14 has a container 59 in which air and cleaning water are contained. Air tube 60 communicated with air in container 59 at one end thereof and water tube 61 communicated with water in container 59 at one end thereof are extended from container 59. Water supply connector 62 detachable to water supply base 16 is attached to the other ends of these tubes. Water supply connector 62 is also of the double cylinder type, corresponding to water supply base 16, and it has therefore a center passage for supplying cleaning water and a ring-shaped passage formed round the center passage to supply air. When water supply connector 62 is connected to water supply base 16, therefore, tubes 32 and 60 are communicated with each other and tube 61 which is communicated with the cleaning water at one end thereof is communicated with upstream side section 11a of the water supply tube.

Figure 3:
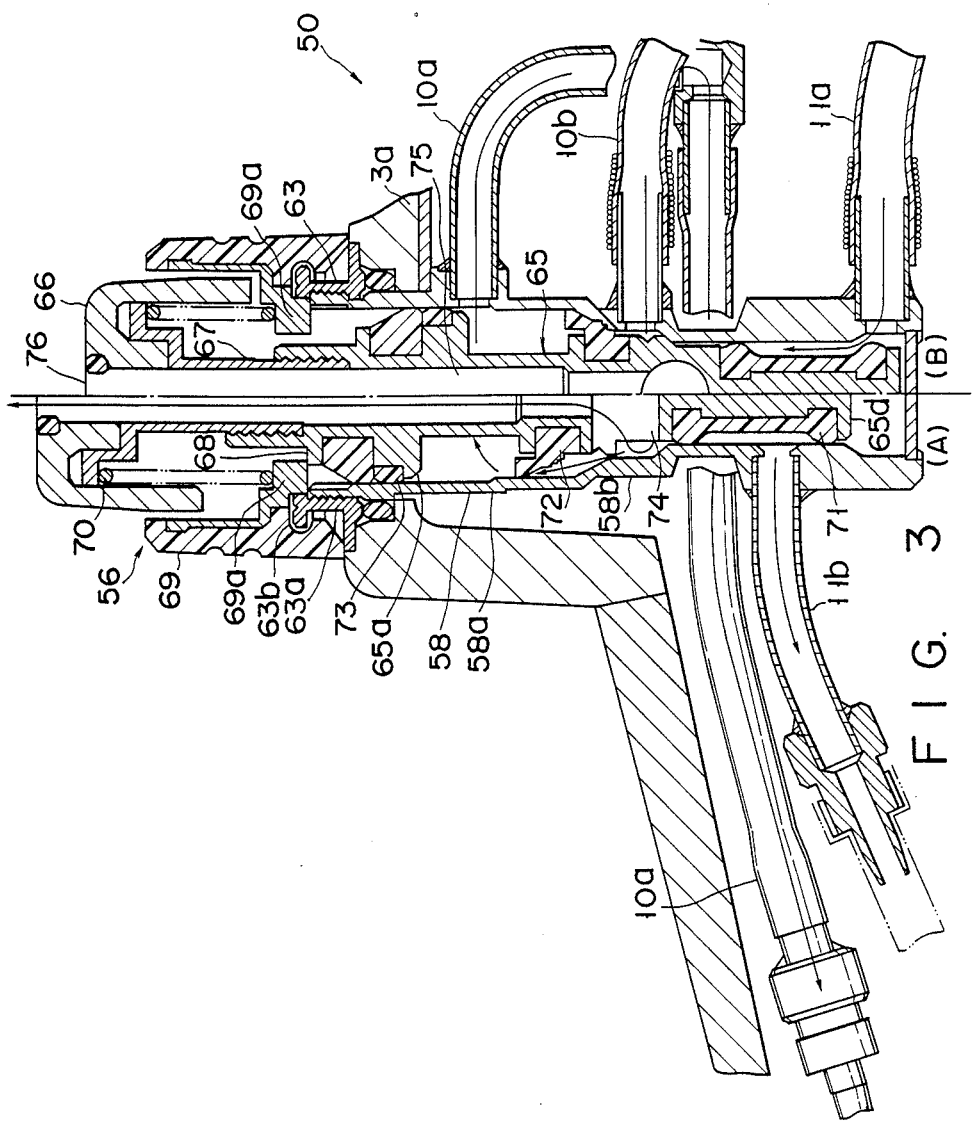
FIG. 3 is a sectional view showing a switch valve of the endoscope for switching air and water wherein the switch valve is kept ready (A) at the left of a dot and dash center line in FIG. 3 while it is under water supply (B) at the right of the line.

Switch valve 50 will be described referring to FIGS. 3 through 5. As shown in FIG. 3, valve seat 58 to which each of valve assemblies 56 and 57 can be attached has a stepped cylindrical shape comprising section 58a provided with an inner hole of large-diameter and section 58b provided with an inner hole of small-diameter. Section 58b of valve seat 58 is located inward in relation to casing 3a of operating section 3 and the end of section 58a projected outward is screwed into ring 63 and casing 3a. Ring 63 includes cylindrical portion 63a having a diameter a little larger than that of the conventional ones, and flange portion 63b formed on the top of this cylindrical portion.

Downstream side tube 10a of air supply tube 10 is communicated with the inner hole in section 58a of valve seat 58, and upstream side tube 10b of the air supply tube, upper and lower side tubes 11a and 11b of the water supply tube which are separated from one another in the axial direction of switch valve 50 are communicated with the inner hole in section 58b.

First valve assembly 56 includes piston 65 slidable therein, connecting pipe 67 connected to the upper end of this piston, operating button 66 connected to the upper end of this connecting pipe, and attachment 69 detachable from flange 63b of the ring. Piston 65 has hollow shaft portion 65 mainly located in section 58a of the valve seat and provided with inner hole 75, and solid shaft portion 65b mainly located in section 58b. Shaft portion 65a has flange 68 projected outward in the radial direction from the upper outer circumference thereof, and opening 74 radially directed adjacent to shaft portion 65b and communicated with inner hole 75. Further, seal ring 71 which is thicker at both ends thereof is arranged round the outer circumference of solid shaft portion 65b of the piston and lip seal 72 and seal ring 73 are arranged round hollow shaft portion 65. Lip seal 72 is contacted with the inner wall of valve seat 58 and serves as the check valve for allowing fluid to flow upward but stopping it from flowing downward.

Connecting pipe 67 enables inner hole 75 of the piston to be communicated with escape hole 76 formed in operating button 66.

Compression spring 70 is arranged between flange 69a of attachment 69, which is projected inward in the radial direction, and operating button 66, and when valve assembly 56 is attached, piston 65 is urged by this spring in such a way that flange 68 is contacted with flange 69a of the attachment, as shown left the dot and dash center line in FIG. 3.

When switch valve 50 is kept ready as shown by (A) in FIG. 3, air flowed through tube 10b can be escaped outside through a clearance between the inner wall of valve seat 58 and the outer circumference of piston 65, opening 74 of the piston, inner hole 75, connecting pipe 67 and escape hole 76 in the operating button. Tube 11b is shielded this time from both of tubes 10b and 11a by both thicker ends of seal member 71. Further, when escape hole 76 in the operating button is closed under this state by a finger of the operator, air flowed through tube 10b and not escaped deforms the rim of lip seal 72 inward in the radial direction and flows into tube 10a through a space between seal members 72 and 73, thereby enabling air to be supplied to liquid supply tube 6a (FIG. 1).

When operating button 66 and piston 65 are pushed against spring 70 under such condition of supplying water as shown by (B) at the right of the center line in FIG. 3, upper and lower side tubes 11a and 11b of the water supply tube are communicated with each other while upper and lower side tubes 10a and 10b of the air supply tube are shielded between them by valve assembly 56. The pressure of air in container 59 of the water supply tank shown in FIG. 1 is thus increased to supply cleaning water to liquid supply tube 6a through water supply tube 11.

Second valve assembly 57 will be described with reference to FIGS. 4 and 5.

Valve assembly 57 includes water switching piston 80 having an inner blind hole and such an outer diameter that enables it to be inserted into valve seat 58, and gas switching piston 81 movable in the inner hole of piston 80. Water switching piston 80 consists of first piston portion 80a having a solid section to which seal ring 82, similar to the one of valve assembly 56, is attached and a hollow section in which valve chamber 83 is defined by gas switching piston 81; and second piston portion 80c connected to the outer end of piston portion 80a and having ring-shaped valve seat 80b projected inward in the radial direction. Connecting pipe 80d is connected to the outer end of second piston portion 80c and cylindrical operating button 84 is connected to the outer end of this connecting pipe. Further, projection 85 is erected from the outer circumference of second piston portion 80c which is adjacent to connecting pipe 80d.

Similarly to first valve assembly, second valve assembly 57 has attachment 86 detachably attached to flange 63b of ring 63. Attachment 86 has flange 86a projected inward in the radial direction and this flange supports spring 87 which urges water switching piston 80 upward through operating button 84. Water switching piston 80 which is urged upward by spring 87 is held as shown at the left of the dot and dash center line in FIG. 4 because projection 85 is contacted with flange 86a of the attachment.

Gas switching piston 81 has a solid portion adjacent to water supply piston 80 and a hollow portion opposite to water supply piston 80, and valve member 88 which cooperates with valve seat 80b of the water switching piston to form a switch valve is attached to the end of the solid portion, while seal ring 102 which is against the inner wall of piston 80 is attached to the hollow portion. Piston 81 is inserted into second piston 80c through a center opening of operating button 84 and connecting pipe 80d and it can move in the axial direction in second piston 80c. Valve member 88 is arranged in valve chamber 83. Compression spring 90 is located between the shoulder of connecting pipe 80d and operating button 89 attached to the outer end of piston 81, and piston 81 is urged upward by this spring 90. Valve member 88 is contacted with valve seat 80 to thereby close a center opening of ring-shaped valve seat 80b. When operating button 89 is pushed downward against spring 87, valve member 88 is separated from valve seat 80b and the center opening of valve seat 80b is communicated with valve chamber 83. Apparently, spring 87 has a rigidity larger than that of spring 90 and when operating button 89 is pushed, piston 81 and then piston 82 are moved downward. Arranged between pistons 81 and 82 are stoppers 91a and 91b for stopping valve member 88 from being unnecessarily deformed when high pressure gas is supplied.

The construction for switching the liquid tube in second valve assembly 57 will be described below.

The circumferential wall of piston portion 80a of the water switching piston is provided with first radially-directed hole 92 at the most inward end of its hollow section and this hole 92 communicates valve chamber 83 with a space outside the outer circumference of piston portion 80a. Similarly, the circumferential wall of second piston portion 80c is provided with second radially-directed hole 93 for communicating its inner hole with a space outside its outer circumference. The spaces outside the outer circumferences of piston portions 80a and 80c can be thus communicated with each other through valve chamber 83, the center opening of valve seat 80b and the inner hole of piston portion 80c. Further, gas switching piston 80 has seal ring 94 on its outer circumference outside first radially-directed hole 92 and adjacent thereto, seal ring 95 outside second radially-directed hole 93 and adjacent thereto, and seal ring 96 between tubes 10a and 10b of the valve seat.

Figure 4:
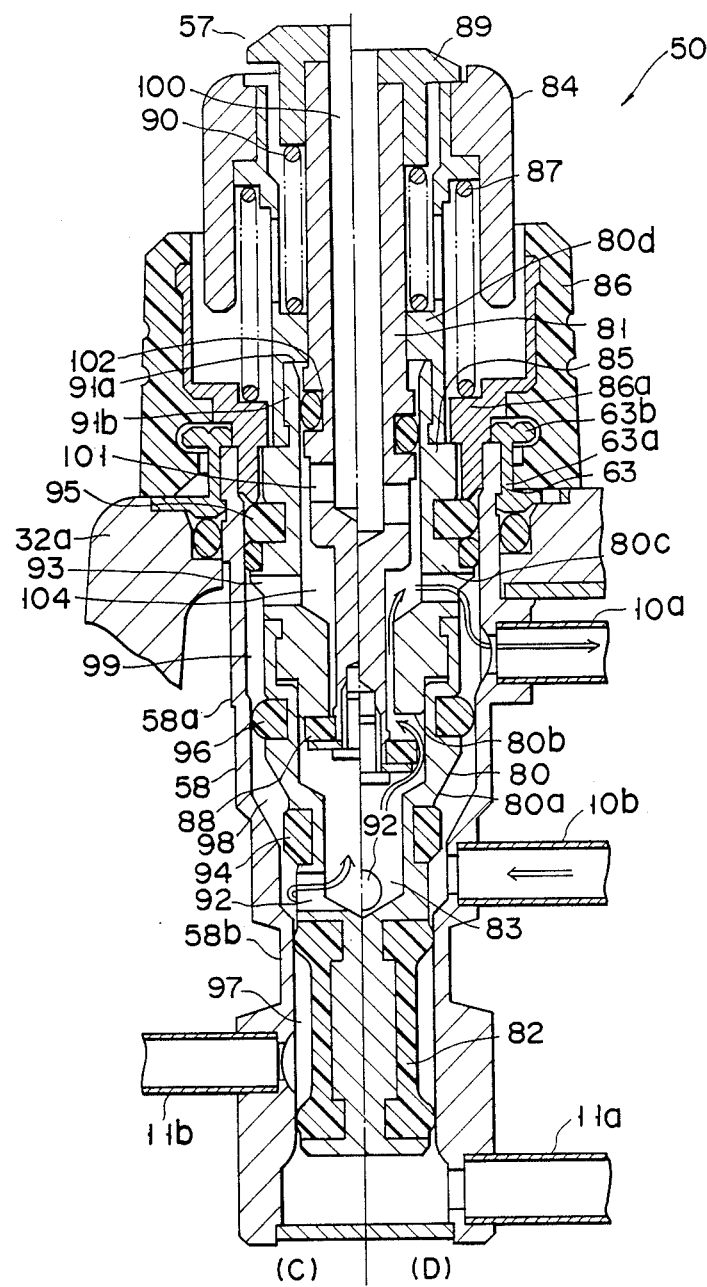
FIG. 4 is a sectional view showing a switch valve of the endoscope for switching gas and water wherein the switch valve is kept ready (C) at the left of a dot and dash center line in FIG. 4 while it is under gas supply (D) at the right of the line.

Second valve assembly 57 is usually kept ready by springs 87 and 90, as shown by (C) at the left of the dot and dash center line in FIG. 4. When second valve assembly 57 is under this state (C), shoulder 85 of piston 80 is contacted with flange 86a of the attachment and stopper 91b of piston 81 is contacted with stopper 91a of piston 80. These pistons 80 and 81 are pushed the most outward in the axial direction and the center opening of valve seat 80b of piston 80 is closed by valve member 88. Seal rings 82, 95 and 96 on the outer circumference of piston 80 are sealingly contacted with the inner face of valve seat 58. Therefore, water chamber 97 which is shielded from tube 11a and gas chambers 98 and 99 which are shielded from each other by valve member 88 are formed between valve seat 58 and piston 80. Nothing is supplied to liquid supply tube 6a (FIG. 1) under this state.

When operating button 89 is pushed to create such condition of supplying gas as shown by (D) at the right of the dot and dash center line in FIG. 4, valve member 88 is separated from ring-shaped valve seat 80b and gas chambers 98 and 99 are communicated with each other through the center opening. Tubes 10a and 10b are thus communicated with each other.

Figure 5:
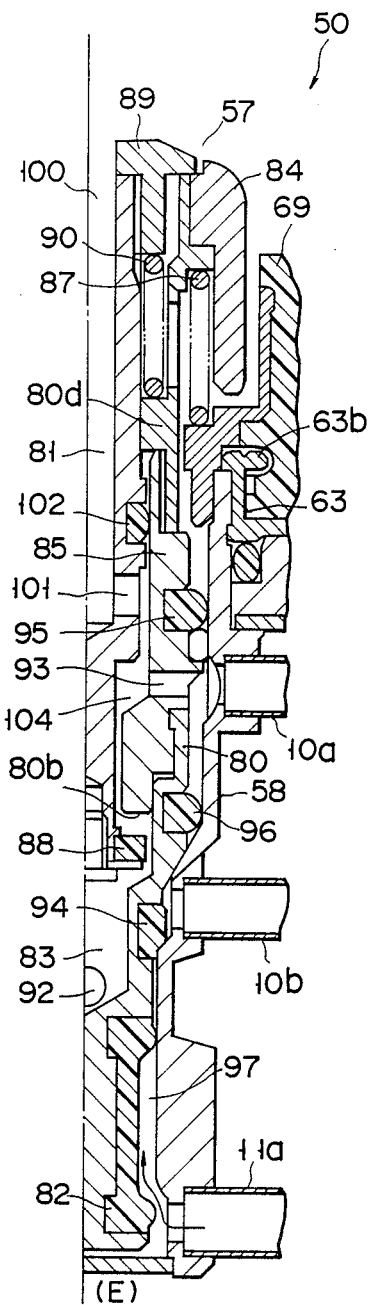
FIG. 5 is a sectional view showing the switch valve in FIG. 4 kept under water supply.

When operating button 89 is further pushed together with operating button 89 to create such condition of supplying water as shown by (E) in FIG. 5, water chamber 97 which is communicated with tube 11b is made communicated with upper side tube 11a. At the same time, seal ring 94 is contacted with the inclined inner face of valve seat 58 to shield first radially-directed hole 92, which is communicated with valve chamber 83, from tube 10b. In addition, tubes 10a and 10b which have been communicated with each other through a clearance between the outer circumference of piston 80 and the inner wall of valve seat 58 are shielded from each other by seal ring 96. Gas flow between tubes 10a and 10b is thus completely shut off and the switching of gas to water is completed accordingly.

Second valve assembly 57 further includes a gas escaping passage. As shown in FIGS. 4 and 5, this escape passage is formed by space 104 between the inner circumferential face of piston portion 80c of the water supply piston and the outer circumferential face of the solid portion of gas supply piston 81, radially-directed hole 101 at the hollow portion of gas supply piston 81, and inner center hole 100 extended in the gas supply piston and opened outside through the operating button. Gas leaked via valve member 88 and seal ring 96 can be thus escaped outside. This escape passage can be closed when the operator puts his finger on operating button 89.

The manner of using endoscope 1 of the present invention will be described with reference to FIGS. 1 through 5.

When endoscope 1 is used as the common one, first valve assembly 56 is attached to valve seat 58 (FIG. 3). Piston 65 is inserted into the inner hole of valve seat 58 and attachment 69 is fitted onto flange 63b of the ring. Connector 62 of water supply tank 14 is then connected to water supply base 16 and thus to endoscope 1. Air supply base 15 is connected to the light source means (not shown). When the air supply pump is then operated, air is supplied from the air supply pump to lower side tube 10b of the air supply tube through air supply base 15 and switch valve 19.

When valve assembly 56 is kept inoperative or ready as shown by (A) at the left of the dot and dash center line in FIG. 3, air leaks outside from tube 10b through radially-directed hole 74 and inner hole 75. Lip seal 72 is not deformed this time and no air flows to tube 10a.

When the operator closes opening 76 by his finger, air can be normally jetted through the foremost end of the inserted section. More specifically, when opening 76 is closed, the rim of lip seal 72 is deformed inward in the radial direction by the pressure of air closed, so that air can flow to lower side tube 10a through the clearance between the rim of lip seal 72 and the inner wall of valve seat 58.

When operating button 66 is further pushed, while closing opening 76, to create such water supplying condition as shown by (B) at the right of the dot and dash center line in FIG. 3, air from tube 10a is shut off and lip seal 72 is contacted with the inclined inner wall. Air is thus shielded from tube 10a and upper and lower side cleaning water supply tubes 11a and 11b are communicated with each other via the outer circumference of seal ring 72 at the same time. Air whose pressure is increased in tube 10b pressurizes cleaning water in container 59 through tube 60, so that the cleaning water can be supplied into water supply tube 11 through tube 61.

When gas and water are to be supplied instead of the above-described air and water supply, second valve assembly 57 is attached to valve seat 58 according to the same manner as in the case of first valve assembly 56 (FIG. 4). Connector 35 is then connected to gas supply base 17 and gas bomb 20 is thus connected to endoscope 1, as shown in FIG. 1. The passage is thus switched through switch valve 19 and gas bomb 20 is communicated with air supply tube 10. When switch valve 47 is then opened, the preparation for supplying water and gas is finished.

When second valve assembly 57 is kept ready as shown by (C) in FIG. 4, communication is shut off between tubes 10b and 10a because valve member 88 is seated on valve seat 80b, and gas such as noninflammable carbon dioxide in the gas bomb is not supplied to lower side tube 10a. Communication is also shut off between cleaning water supply tubes 11a and 11b by seal ring 82 and no cleaning water is jetted through the foremost end of the inserted section.

When second valve assembly 57 is under gas supplying condition as shown by (D) in FIG. 4 and operating button 89 is pushed while closing opening 100, piston 81 is lowered, valve member 88 is separated from ring-shaped valve seat 80b, and valve chamber 83 and space 104 are communicated with each other through the center port of valve seat 80b. Carbon dioxide in the gas bomb is thus fed from upper side tube 10b to lower side tube 10a through hole 92, valve chamber 83 and space 104. Gas is not allowed to flow outside because opening 100 is closed by finger.

When second valve assembly 57 is under water supplying condition as shown by (E) in FIG. 5 and operating button 84 is pushed, opening 92 is shielded from tube 10b by seal ring 94 and water supply tubes 11a and 11b are communicated with each other at the same time. The cleaning water in the water supply tank is thus pressurized and supplied to water supply tube 11 (FIG. 1), as described above in the common case.

Generally speaking, there is the fear that the pressure in the gas bomb is set higher than needed when the endoscope is being used. When the gas pressure is set high like this and it is so high as to overcome the sealing capacity of seal rings, or when the rings and valve member are deteriorated or damaged (it is difficult to completely prevent these rings from being damaged even if that end of each of tubes which is opened at the inner face of the valve seat is chamfered to prevent the rings from being damaged at the time when the valve assembly is attached or detached), or when valve member 88 is not returned completely because of some faults, there is the fear in the conventional endoscopes that highly-pressurized gas is leaked into the outlet tube.

Even when the above-mentioned trouble is caused in the case of endoscope 1 of the present invention, it can be overcome because the escape passage is formed at the lower side of valve member 88 and seal ring 96. Namely, gas flowing into gas chamber 99 and space 104 can be leaked outside through inner hole 100. This is because the resistance in the escape passage is smaller than that in the lower side tube. The endoscope can be thus operated with safety at all times. Further, gas and air sources can be easily switched when connector 35 is attached to gas supply base 17.

Figure 6:
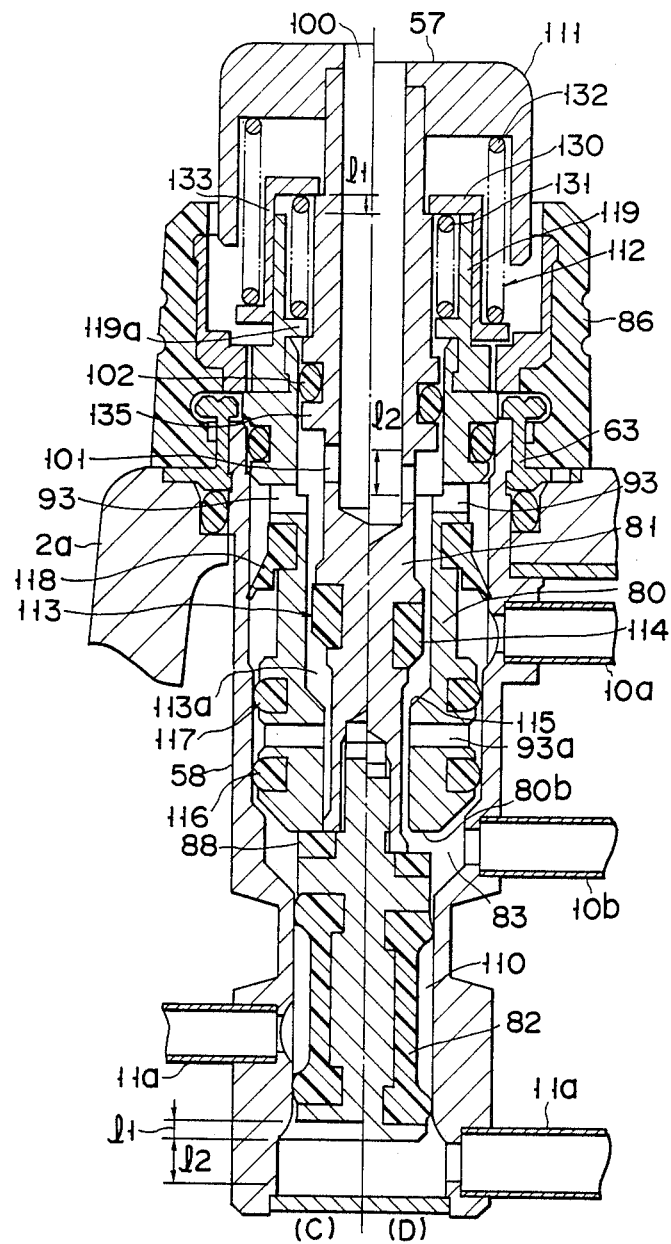
FIG. 6 is a view similar to FIG. 4, showing a first variation of the gas and water switching valve.
Figure 7:
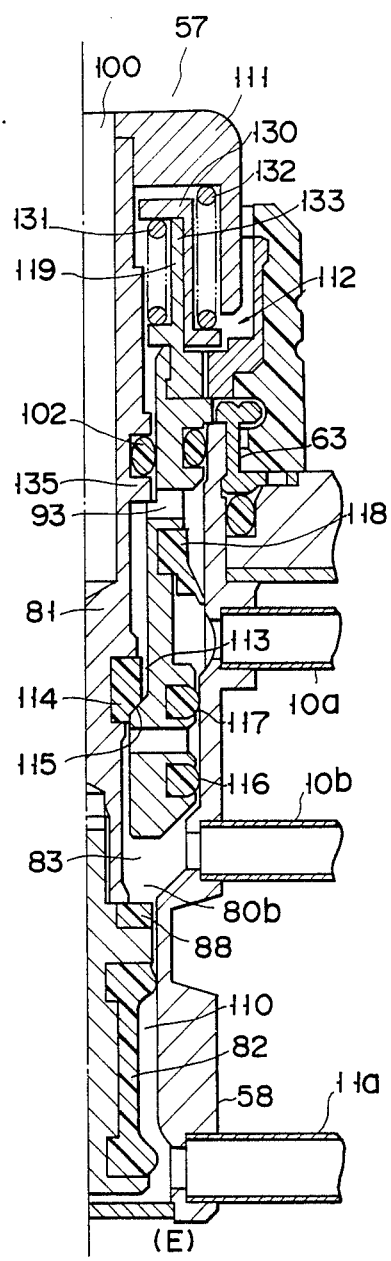
FIG. 7 is a view similar to FIG. 5, showing the first variation of the gas and water switching valve.

FIGS. 6 and 7 show a variation of second valve assembly 57.

This variation of second valve assembly 57 is different from that in the first example of the endoscope and valve member 88 is located inward the foremost end of piston 80 when seen in the axial direction.

In the case of this variation of second valve assembly 57, piston foremost end portion 110 having seal ring 82 similar to that in the first example of the endoscope is located in front of hollow piston 80 (or inward the foremost end of hollow piston 80 when seen in the axial direction) which is provided with valve seat 80b. Valve member 88 is attached to piston foremost end portion 110, corresponding to valve seat 80b. Hollow operating button 111 is attached to the top of piston 81 which is inserted into and projected from piston 80. Slider mechanism 112 which operates in two-step manner is arranged between operating buttons 111 and 66. Further, switch valve 113 (consisting of valve member 114 and valve seat 115) is attached to the shaft portion of piston 81, and seal rings 116, 117 and stopper or check valve 118 (which are contacted with the inner face of valve seat 58) are arranged round the outer circumference of piston 80 in this order from below so as to make it possible to switch the flow passage.

Slider mechanism 112 comprises cylindrical wall 119 fitted onto the shaft portion of piston 80 right under operating button 111 and connected to ring 86, and cylindrical slider 130 slidably mounted on the end portion of cylindrical wall 119. Compression spring 131 is arranged between the spring seat of cylindrical wall 119 and the ceiling of slider 130 and another spring 132 which is stronger than spring 131 is arranged between a spring seat formed round the outer circumference of slider 130 and the ceiling of operating button 121, thereby lifting piston 81 to the level of stopper 119a of cylindrical wall 119. In addition, piston 81 is successively pushed down by distance l1 and then by distance l2, using two stoppers 134 and 135. In other words, the amount l1 of piston 81 pushed is determined by compression spring 131 and the amount l2 of piston 81 further pushed is determined by compression spring 132. The operator can operate operating button 111, feeling the difference between l1 and l2 by his finger.

When this variation of second valve assembly 57 is kept ready as shown by (C) at the left of the dot and dash center line in FIG. 6, valve member 88 is closely contacted with valve seat 88b to shield lower side tube 10a, and upper side tube 10b is shielded by seal rings 82 and 116. Water supply tube 11 is shielded by seal ring 82, as described in the case of the first example of the endoscope.

When this version is under such gas supplying condition as shown by (D) at the right of the dot and dash center line in FIG. 6, and piston 81 is pushed down by l1, valve member 88 is separated from valve seat 80b and valve chamber 83 under piston 80 is communicated with valve chamber 113a of switch valve 113. Gas can be fed from upper side tube 10b to lower side tube 10a under this state.

When it is under such water supplying condition as shown by (E) in FIG. 7, piston 81 is pushed down by l2 and valve member 114 of switch valve 113 is contacted with valve seat 115 to thereby shut off the gas communication between valve chambers 83 and 113a. Further, the lower end of seal ring 82 is separated from the inner wall of valve seat 58 and tubes 11a and 11b are communicated with each other. Water is thus fed from the water supply tank to tube 11.

Piston 81 in this version has holes 100 and 101 in its shaft portion to form an escape passage similar to that in the first example of the endoscope, and these holes are communicated with leak passages at the lower sides of valve member 114 and seal ring 116. When the gas pressure is mistakenly set high, therefore, gas which is so high in pressure as to overcome the sealing capacity of the seal ring can be escaped into the atmosphere. When this version is kept ready as shown by (C) at the left of the dot and dash center line in FIG. 3 and the gas pressure in tube 10b is so high as to overcome the sealing capacity of seal ring 116, gas escapes into the atmosphere (or outside the endoscope) through hole portion 93a between seal rings 116 and 117, valve chamber 113a of switch valve 113, hole portion 101 and leakage passage 100. Apparently, gas leaked via valve member 88 can also escape through hole 101 and leakage passage 100 when this version is kept ready. Even when both of seal rings 116 and 117 are damaged or not closely contacted with the inner face of valve seat 58, gas can also escape.

Check valve 118 is arranged between hole 93 and tube 10a in the case of this version. Flow is thus allowed only from the upper side to the lower side and backward flow from lower side tube 10a is stopped accordingly. This is therefore advantageous to the backward flow of matters in the cavity of the human body and the backward flow of water caused when pressurized water supply is being carried out through an auxiliary water supply opening on the way of water supply tube 11, using a syringe. Further, this version can have a longer life because seal rings 102, 116, 117 and check valve 118 are not slid relative to valve seat 58 when the endoscope is under use.

Figure 8:
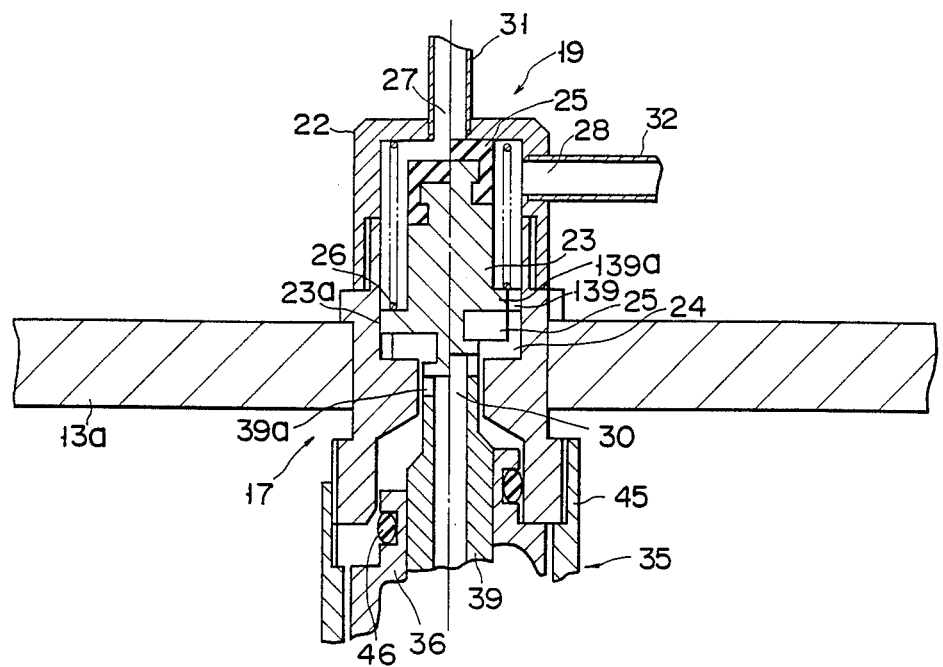
FIG. 8 is a view similar to FIG. 2, showing a first variation of the gas supply base.

FIG. 8 shows a variation of switch valve 19 in base 17.

This variation of switch valve 19 is provided with air inlet and outlet ports 27 and 28 in the ceiling and side of housing 22, enabling air and gas to be automatically switched by piston 23.

In the case of this variation, valve member 25 is located on the upper end of piston 31 and air inlet port 27 which corresponds to this valve member and which is communicated with tube 31 is formed in the ceiling of housing 22. When gas connector 35 is connected to base 17 as described above in the first example of the endoscope, ports 30 and 28 are communicated with each other. Numeral 139 in FIG. 8 denotes a communication hole formed in flange 139a to partition valve chamber 24 into two chambers.

FIG. 9 shows a second variation of second valve assembly under water supplying condition (E), wherein the check valve is different in construction from that in the first variation shown in FIGS. 6 and 7.

In the case of this second variation of second valve assembly 57, piston 80 has plural radially-directed through-holes 120 in its circumferential wall. Ring-shaped groove 121 is formed round the outer circumference of piston 80 at which through-holes 120 are opened, and valve member 122 made of cylindrical rubber is fitted into this ring-shaped groove 121 and serves as check valve 118.

Check valve 118 in this variation keeps valve member 122 untouched with valve seat 58 when valve assembly 57 is attached, thereby preventing valve member 122 from being damaged.

Figure 10:
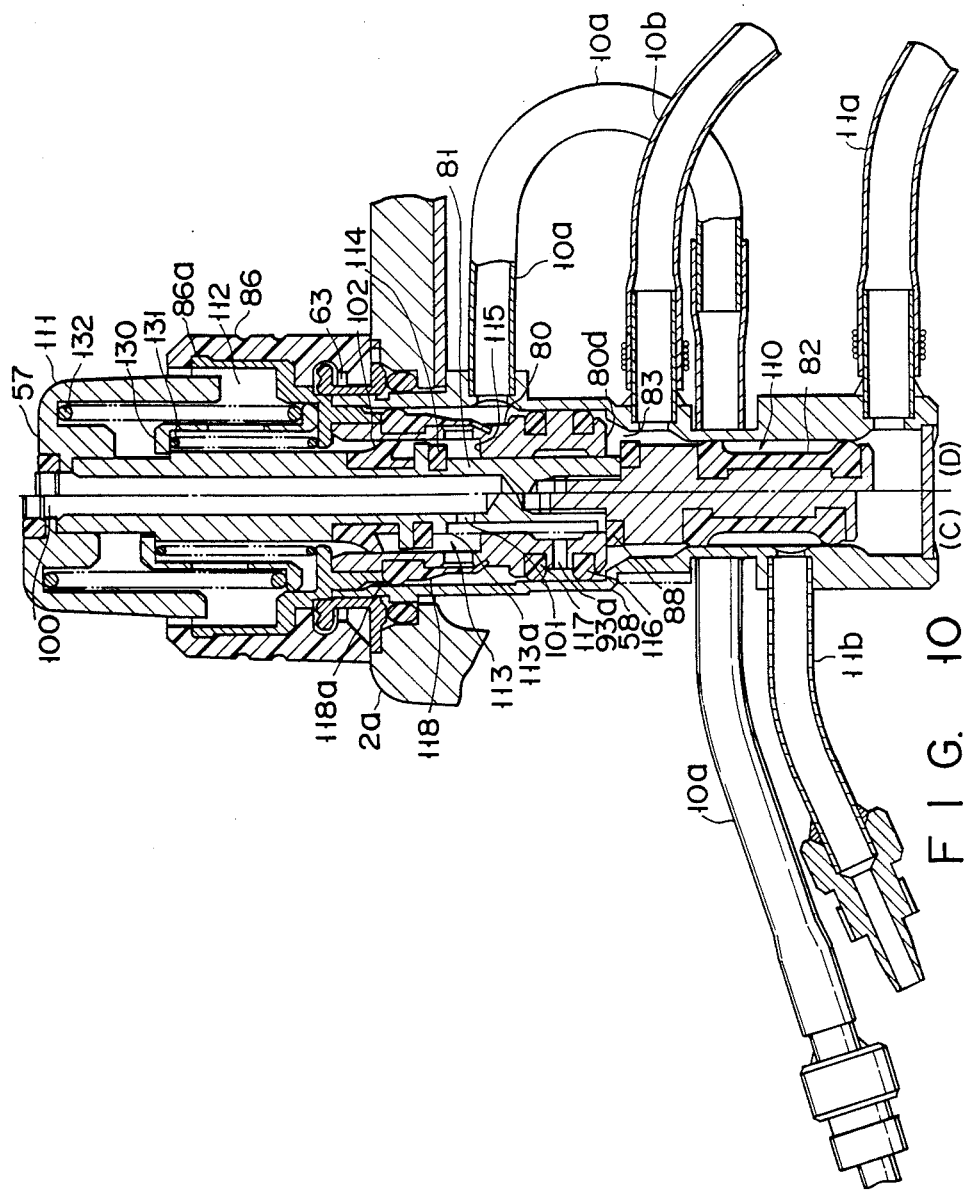
FIGS. 10 and 11 are views similar to FIGS. 4 and 5, showing a third variation of the gas and water switching valve.
Figure 11:
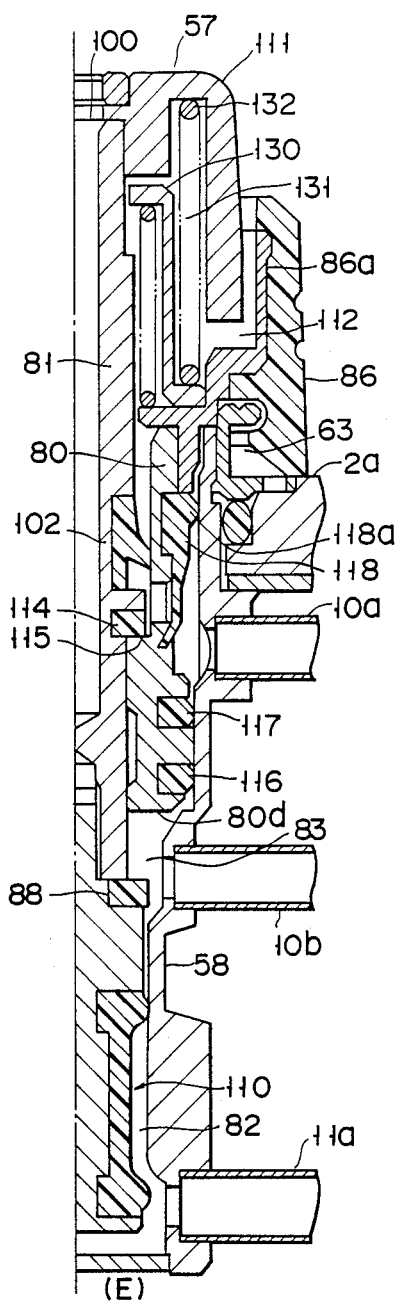

FIGS. 10 and 11 show a third variation of second valve assembly under ready condition (C), gas supplying condition (D) and water supplying condition (E). Slider mechanism 112, check valve 118, seals of piston 81 and switch valve 113 in this variation are different in construction from those in the first variation.

In the case of this third variation of second valve assembly 57, fixing member 86a which is located inside attachment ring 86 is formed integral to the top of piston 80, as shown in FIGS. 10 and 11. Cylindrical wall 119 in the first variation (see FIG. 6) can be thus omitted, thereby enabling operating button 111 to be smaller-sized.

Check valve 118 has an elongated upper end portion and sealing projection 118a projected from the outer circumference of this elongated portion. This check valve 118 also serves as the member for sealing between the outer circumference of piston 80 and the inner circumference of valve seat 58 just above check valve 118 in the first variation shown in FIG. 6. This means that check valve 118 is made also to serve as a seal between piston 80 and valve seat 58, so that it can be smaller-sized with lower cost. Further, it can be assembled with more easiness.

Piston 81 has such a sealing arrangement that seal ring 102 arranged round the shaft portion of piston 81 is formed as an umbrella-shaped valve member and that this umbrella-shaped valve member is arranged just above valve member 114 of piston 81. This umbrella-like valve and seal member arranged just above valve member 114 enables inner hole 100 to be made longer and hole 101 to be formed just below valve member 114. The sliding resistance of piston 81 can be thus made smaller.

Switch valve 113 is made in such a way that the seat member receives valve member 114 not with a tapered face but with a flat face. More specifically, valve member 114 used has a flat underside and valve seat 115 which is combined with valve member 114 has a flat seat face, so that the opening and closing operation can be achieved by contact and separation of these flat faces.

This switch valve 113 can prevent valve member 114 from biting into valve seat 115, thereby enabling their durability (or life) to be enhanced. Further, the accuracy of that position where valve member 114 is struck against valve seat 115 can be enhanced. This can be confirmed by the amount of piston 81 moved. More specifically, when valve member 114 is struck against valve seat 115, the rubber of which valve member 114 is made is deformed, but the amount of piston 81 moved by this rubber deformation can be made smaller when valve member 114 has a flat underside than when it has a tapered face.

Figure 12:
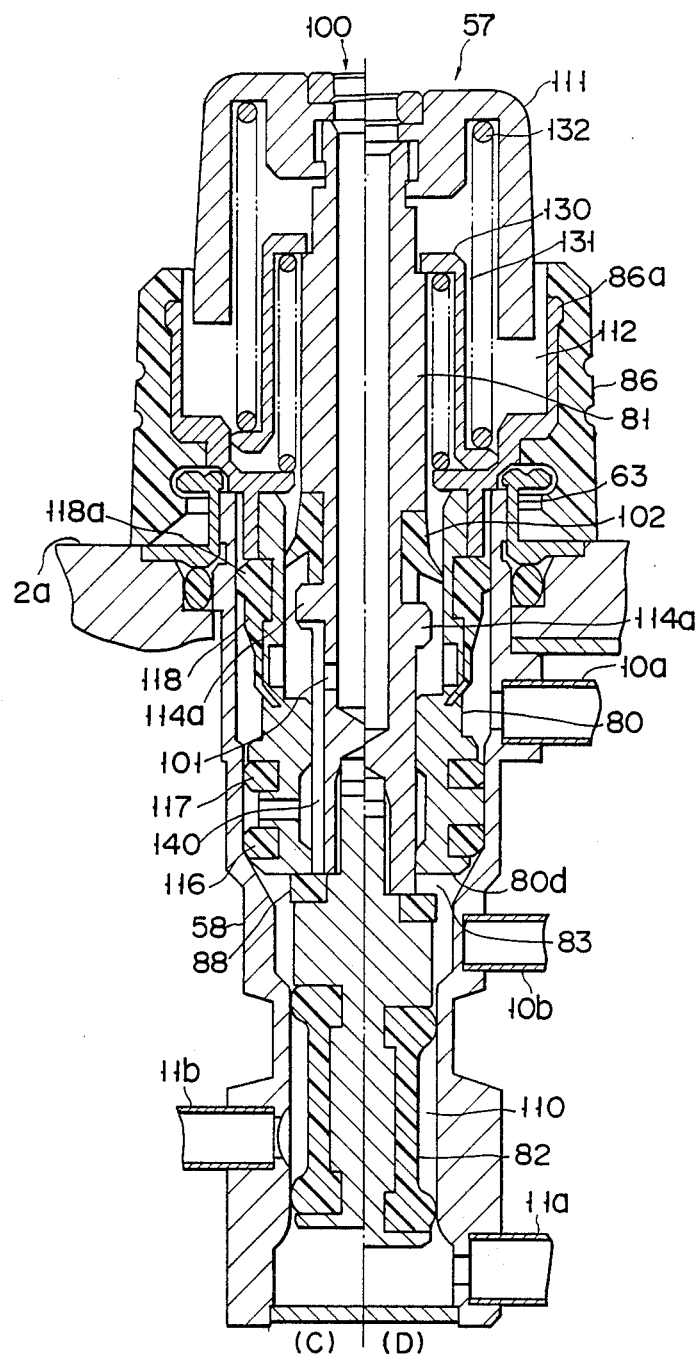
FIGS. 12 and 13 are views similar to FIGS. 4 and 5, showing a fourth variation of the gas and water switching valve.
Figure 13:
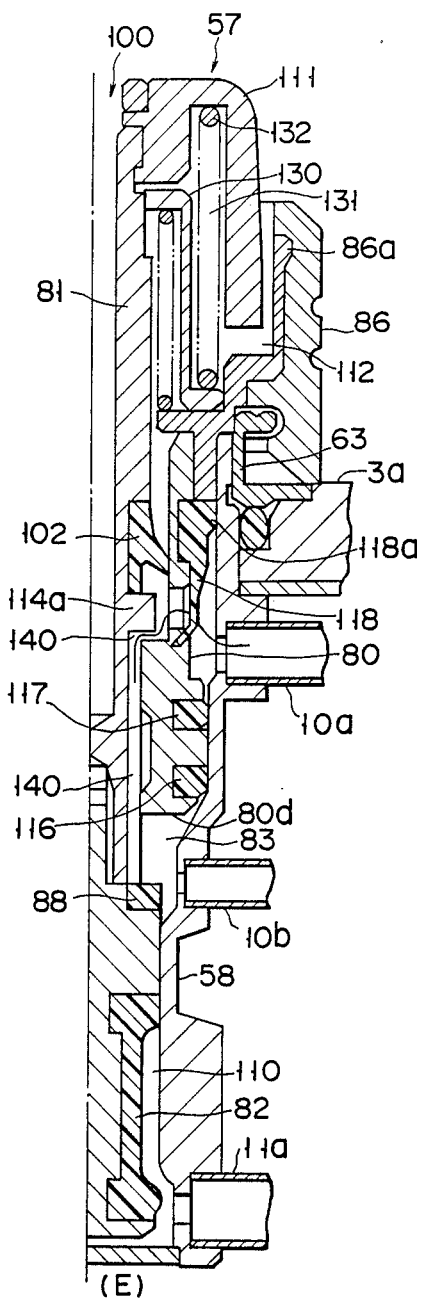

FIGS. 12 and 13 show a fourth variation of second valve assembly 57 under ready condition (C), gas supplying condition (D), and water supplying condition (E). In the case of this fourth variation, valve member 114 in the third variation (FIGS. 10 and 11) is omitted, but support 114a for this valve member is made wider in the axial direction and groove 140 is formed in the axial direction and along the outer circumference of that portion of piston 81 which extends downward from the underside of support 114a.

When this fourth variation is under water supplying condition (E) as shown in FIG. 13, a part of gas is supplied to lower side tube 10a through groove 140 and a mixture of water and gas can be thus supplied like spray.

Figure 14:
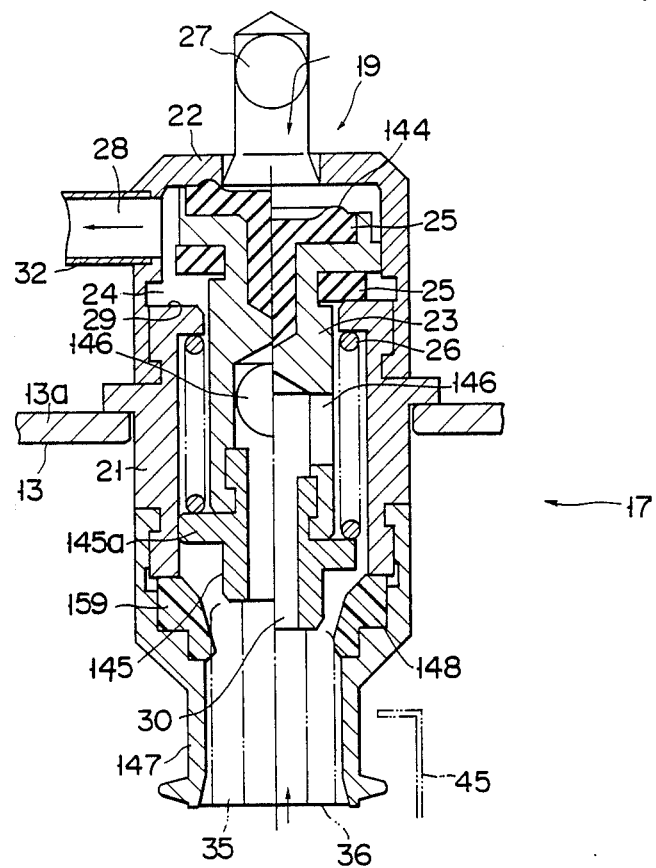
FIG. 14 is a view similar to FIG. 2, showing a second variation of the gas supply base.

FIG. 14 shows a second variation of switch valve 19. In the case of this second variation, valve member 25 which is formed on the middle of piston 23 in the example shown in FIG. 2 is now formed on the top of piston 23 and valve seat 29 which is the end face of base member 21 is extended inward in the radial direction.

As shown in FIG. 14, ring-shaped seal 144 is formed on the end face of valve member 25 to contact the circumferential rim portion of air inlet port 27 and compression spring 26 is arranged between flange 145a of cylindrical receiving member 145 connected to the foremost end of piston 23 and a stepped portion formed just under the valve seat of base member 21.

Valve member 25 of piston 23 is therefore usually separated from valve seat 29 to communicate the passage formed between air inlet port 27 and outlet port 28 (at the time of air supply). When the foremost end portion of connector 35 is fitted into member 147 which is connected to the foremost end of base member 21, and connector 35 is fixed by ring 45 as described above in the first example, seal 144 of piston 23 is pressed against the circumferential rim of air inlet port 27 to thereby close the passage between ports 27 and 28. Further, hole 146 is formed in the circumferential wall of piston 23 to which receiving member 145 is connected, so that the air intake passage can be shielded when connector 35 is connected while gas can be supplied to port 28 through hole 146 and a clearance between piston 23 and base member 21. The switching of gas and water can be thus achieve by the movement of piston 23, as achieved by the switch valve in the first example. Numeral 148 represents a seal member arranged inside the member 147 and when connector is connected, seal member 148 is contacted with the end of the base member to seal between this base member and the connector. Further, additional hole 146 is formed in the circumferential wall of piston 23 and water remaining in piston 23 at the time of cleaning can be easily discharged through this hole 146.

The above-described embodiment and its related variations can be applied to the endoscopes which use image guide fibers. In addition, they can be apparently applied to those which use solid state pickup elements.

According to the above-described endoscope and its related variations, gas and highly-pressurized gas leaked through the seals to cause various troubles can be escaped outside, thereby preventing too much gas from being supplied to the patient.

A second example of the endoscope will be described referring to FIGS. 15 through 17.

Figure 15:
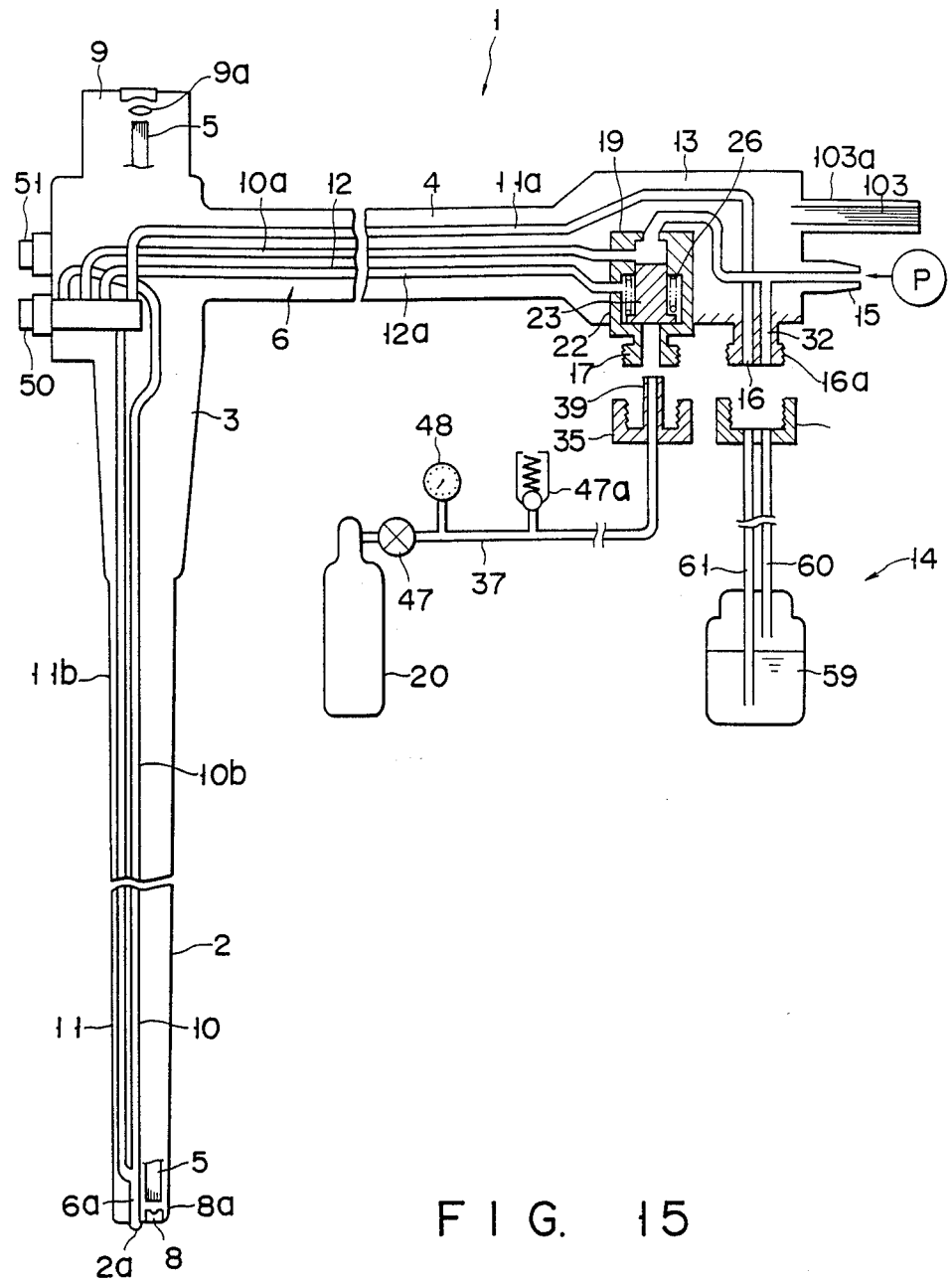
FIG. 15 is a view similar to FIG. 1, showing a second example of the endoscope according to the present invention.

As shown in FIG. 15, endoscope 1 includes section 2 inserted into the cavity of the human body, operating section 3 capable of controlling the insertion section from outside the human body, and universal code 4. Eyepiece 9 is arranged at operating section 3. Connector 13 which can be connected to a light source means (not shown) is arranged at the end of universal code 4. Further, image and light guide fiber bundles 5 and 103 are extended through the endoscope. The foremost end of image guide fiber bundle 5 is optically connected to objective 8a at the foremost end of insertion section 2 and objective 8a is aligned with observation window 8. The foremost end of light guide fiber bundle 103 is optically connected to an illumination window (not shown) at the foremost end of insertion section 2. The back end of light guide fiber bundle 103 is housed in guide pipe 103a of connector 13.

Further, air, water and gas supply tubes 10, 11 and 12 are arranged in endoscope 1. Air supply tube 10 is divided into upper and lower side air supply tubes 10a and 10b by switch valve means 50 at operating section 3. The foremost end of lower side air supply tube 10b is connected to nozzle 2a at the foremost end of insertion section 2. The base end of upper side tube 10a of air supply tube 10 is connected to air supply base 15 at connector 13 of universal code 4. This air supply base 15 can be connected to an air pump which serves to supply pressurized air.

Water supply tube 11 is also divided into upper and lower side tubes 11a and 11b by switch valve means 50 at operating section 3. The foremost end of lower side tube 11b of this water supply tube is connected to nozzle 2a at the foremost end of inserted section 2. The base end of upper side tube 11a is connected to water supply base 16 at connector 13 of universal code 4.

Further, gas supply tube 12 is also divided into upper and lower side tubes by switch valve means 50 at operating section 3, but lower side tube 10b of air supply tube 10 serves as this lower side gas supply tube in this example. Therefore, the foremost end of lower side tube of gas supply tube 12 is also connected to nozzle 2a at the foremost end of insertion section 2. The base end of upper side tube 12a is connected to gas supply base 17 at connector 13 of universal code 4.

Water supply base 16 is formed as water supply tank receptor 16a at connector 13 and branch tube 32 which is communicated with tube 10a halfway is connected to this receptor. Further, connector 62 of the water supply tank can be detachably attached to receptor 16a. Tubes 60 and 61 are connected to water supply tank connector 62, and they are communicated with water (or cleaning water) and air in container 59, respectively, when connector 62 is attached to receptor 16a.

Switch valve 19 for selecting either air or gas is incorporated into connector 13. This switch valve 19 includes cylindrical housing 22 and piston 23 slidable in the axial direction in housing 22, and upper side air and gas supply tubes 10a and 12a are communicated with the inside of housing 22. Piston 23 is urged downward by coil spring 26. As shown in FIG. 15, piston 23 usually shuts off tube 12a and keeps upper side air supply tube 10a communicated with a chamber on this piston. When piston is pushed against coil spring 26, tube 12a is communicated with port 30 and tube 10a is shut off.

Connector 35 can be detachably attached to gas supply base 17. Piston or operating pipe 39 is erected from the center of gas connector 35. When connector 35 is attached to gas supply base 17, operating pipe 39 pushes piston 23 and the above-described switching operation is automatically carried out. Gas tube 37 is connected to gas connector 35 and communicated with gas bomb 20 in which non-inflammable gas (or carbon dioxide, for example) is contained. Pressure regulating valve 47, pressure gage 48 and relief valve 47a are arranged on the way of tube 37. Numeral 51 in FIG. 15 represents a suction switch valve which is located adjacent to the switch valve means.

The switch valve means 50 employed by the second example of the endoscope will be described with reference to FIGS. 16 and 17.

Switch valve means 50 comprises valve seat (or cylinder) 150, first and second pistons 151 and 152 which are inserted into valve seat 150, and valve seat 150 is fixed to housing 153 of the operating section. More specifically, valve seat 150 is inserted through hole 154 in housing 153 of the operating section and screw seat 155 is then screwed onto an opened end of valve seat 150 to fasten housing 153 together with flange 156 of valve seat 150. Cylinder 157 made of resilient resin is attached to screw seat 155. Cylindrical seat 158 is fixed to the inner circumference of cylinder 157.

First piston 151 is made cylindrical and second piston 152 which has been inserted into first piston 151 is arranged in valve seat 150. The top of first piston 151 is struck from below against first flange 161 projected from the inner circumference of cylindrical seat 158. Spring receiving cylinder 162 is arranged round second piston 152 in receptor seat 158. Spring receiving cylinder 162 has second flange 164 projected inward from the top thereof, and first compression spring 165 is interposed between first and second flanges 161 and 164 to urge spring receiving cylinder 162 upward. Second flange 164 contacts the top of second piston 152 and follows the movement of second piston 152.

Third flange 166 is projected outward from the outer circumference of spring receiving cylinder 162 and the underside of this third flange 166 is struck against stepped portion 167 of receptor seat 158, thereby limiting the movement of spring receiving cylinder 162. Further, connecting pipe 168 is screwed onto second piston 152 and provided with fourth flange 169 on the top thereof. Second compression spring 172 is arranged between fourth and third flanges 169 and 166 to urge second piston upward. Second compression spring 172 has a spring force stronger than that of first compression spring 165 and second piston 152 is therefore urged upward till its top strikes against second flange 164.

Operating button 173 is mounted on the top of connecting pipe 168. Operating button 173 has opening 175 of leak hole 174 which extends through this operating button, connecting pipe 168 and second piston 152. Second piston 152 is longer than first piston 151 and it comprises outer member 176 and inner member 177 connected to the lower end of outer member 176. First valve 181 having a shape like a seal ring is attached to those portions of outer and inner members 176 and 177 where they are connected with each other. The lower end of first piston 151 is struck against this valve 181.

Upper and lower side water supply tubes 11a, 11b, upper side gas supply tube 12a, and upper and lower side air supply tubes 10a, 10b are connected to the circumferential wall of valve seat 150 in this order when seen from below. Their connecting openings face the circumferential face of the first or second piston, except the one for upper side water supply tube 11a. Namely, upper side water supply tube 11a is communicated with a space in the bottom of valve seat 150. The connecting opening of lower side water supply tube 11b faces recessed portion 183 of second cylindrical valve 182 which is fitted round the outer circumference of outer member 177 of second piston 152. The outer circumference of second valve 182 is made smaller in diameter at the medium thereof to form recessed portion 183, which is shielded from the inside of valve seat 150. Inner circumference 185 of valve seat 150 on which projections 184 and 184 are slid is made smaller in diameter than that portion of valve seat 150 which is provided with the connecting opening of upper side water supply tube 11a. Recessed portion 183 of the second valve therefore usually faces only the connecting opening of lower side water supply tube 11b, but when second piston 152 is pushed down further than a predetermined value, recessed portion 183 is communicated with the connecting opening of upper side water supply tube 11a, which is thus communicated with lower side water supply tube 11b through this recessed portion 183. The connecting opening of upper side gas supply tube 12a is communicated with valve chamber 190 between third and fourth valves 185 and 186 which are formed like seal rings round the outer circumference of the lower end of first piston 151. That portion of first piston 151 which are located between third and fourth valves 185 and 186 is provided with through-holes 187 and 187. These through-holes 187 and 187 are communicated with axially-directed grooves 188 and 188 which are formed on the circumference of second piston 152.

The connecting opening of lower side air supply tube 10b which also serves as the lower side gas supply tube faces the outer circumference of first piston 151 above fourth valve 186. Fifth valve 189 which serves as a stopper valve is attached round the outer circumference of first piston 151. Fifth valve 189 covers through-holes 191 and 191 in first piston 151 from outside so as to allow flow from inside to pass through these holes but backward flow to be stopped. Throughholes 191 are communicated with grooves 188.

Sixth valve 192 is attached round the outer circumference of second piston 152 above grooves 188 and struck against the end face of stepped portion 193 which is formed on the inner circumference of first piston 151 below it, when second piston 152 is pushed down. Further, seventh leak stopper valve 194 is attached round the outer circumference of second piston 152 above sixth valve 192 to shield upward flow. That portion of second piston 152 which is between sixth and seventh valves 192 and 194 is provided with through-holes 195 communicated with leak hole 174.

The operation of above-described switch valve means 50 will be described. Air and water supplies are usually carried out and water supply tank connector 62 is connected to water supply base 16 of connector 13 in this case to make it ready to supply water. Further, the air supply pump is connected to air supply base 15 of connector 13. Connector 35 is not connected to gas supply base 17. As shown in FIG. 15, therefore, air and gas switch valve 19 shields gas supply tube 12 but communicates air supply tube 10. Switch valve means 50 at operating section 3 is kept ready as shown by (C) at the left of the dot and dash center line in FIG. 16. First and second pistons 151 and 152 are lifted by first and second springs 165 and 172 and the lower end of first piston 151 is struck against first valve 181 to thereby shield upper side gas supply tube 12a from grooves 188. Since gas is not supplied through upper side gas supply tube 12a in this case, no flow is caused. In addition, upper and lower side water supply tubes 11a and 11b are shielded from each other by second valve 182 and water is not supplied accordingly.

The connecting opening of upper side air supply tube 10a is shielded by third and fourth valves 185 and 186 but communicated with grooves 188 on second piston via through-holes 187 of first piston 151. Further, sixth valve 192 on first piston 151 is separated from the end face of the stepped portion of second piston 152 and air supplied through upper side air supply tube 10a therefore continues to leak outside via through-holes 195 in second piston 152 unless the operator closes opening 175 of leak hole 174 by his finger. Fifth valve 189 is interposed between through-holes 188 and lower side air supply tube 10b and air does not become so high in pressure as to push and open fifth valve 189 thanks to the above-described leakage of air. Therefore, no air flows into lower side air supply tube 10b.

Figure 16:
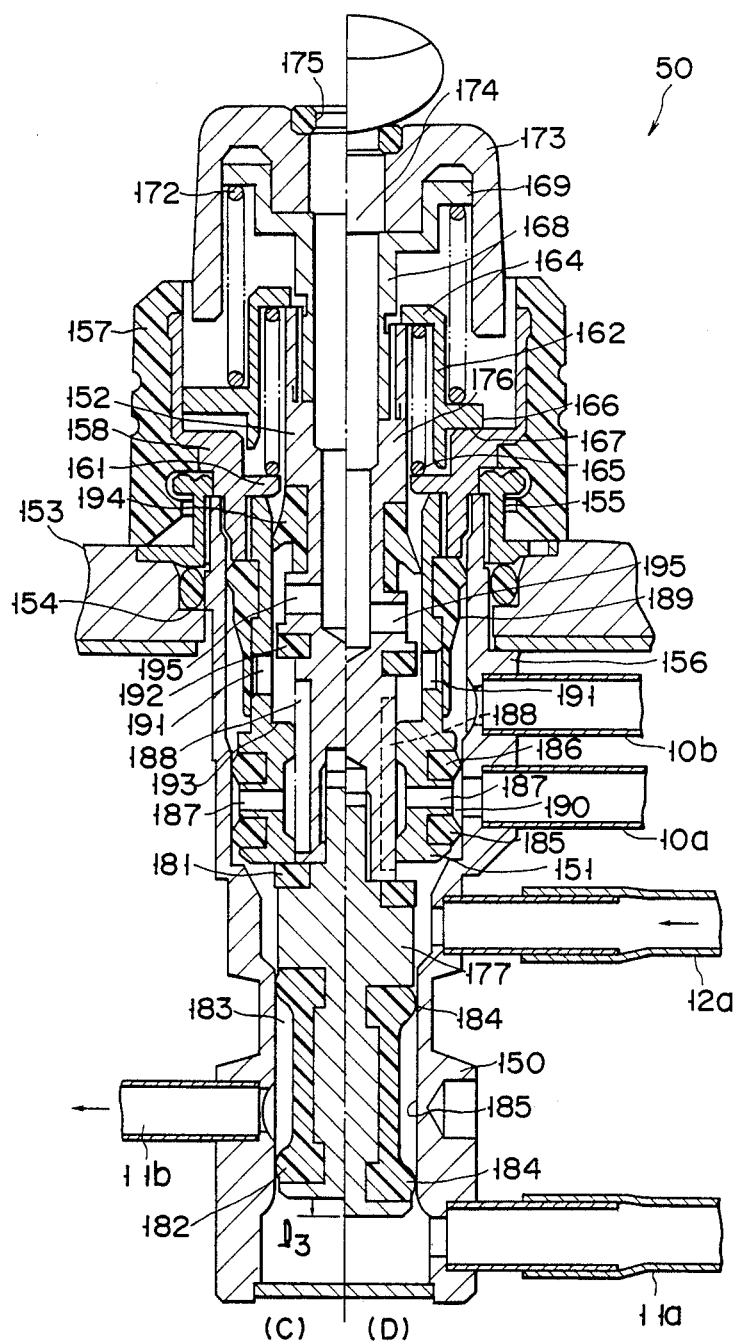
FIGS. 16 and 17 are views similar to FIGS. 4 and 5, showing a gas and water switching valve employed in the second example of the endoscope.

When air is to be supplied, second piston 152 is pushed by l3 while closing opening 175 of leak hole 174, as shown by (D) at the right of the dot and dash center line in FIG. 16. Only first spring 165 which is lower in spring force is compressed and second flange 166 of spring receiving cylinder 162 is struck against the face of stepped portion 167, thereby causing second piston 152 to be stopped. Since leak hole 174 is closed under this state, air supplied through grooves 188 becomes high in pressure to push and open fifth valve 189 and flow into lower side air supply tube 10b, so that air can be supplied to the cavity of the patient through nozzle 2a at the foremost end of insertion section 2. The amount of air supplied can be closely adjusted when the closing of opening 175 of leak hole 174 is adjusted. The lower end of first piston 151 is separated from first valve 181 and grooves 188 are thus communicated with upper side gas supply tube 12a, but since no gas is supplied through upper side gas supply tube 12a as described above, nothing is caused. Upper side water supply tube 11a is shielded from lower side water supply tube 11b by second valve 182 in this case and no water is supplied accordingly.

Figure 17:
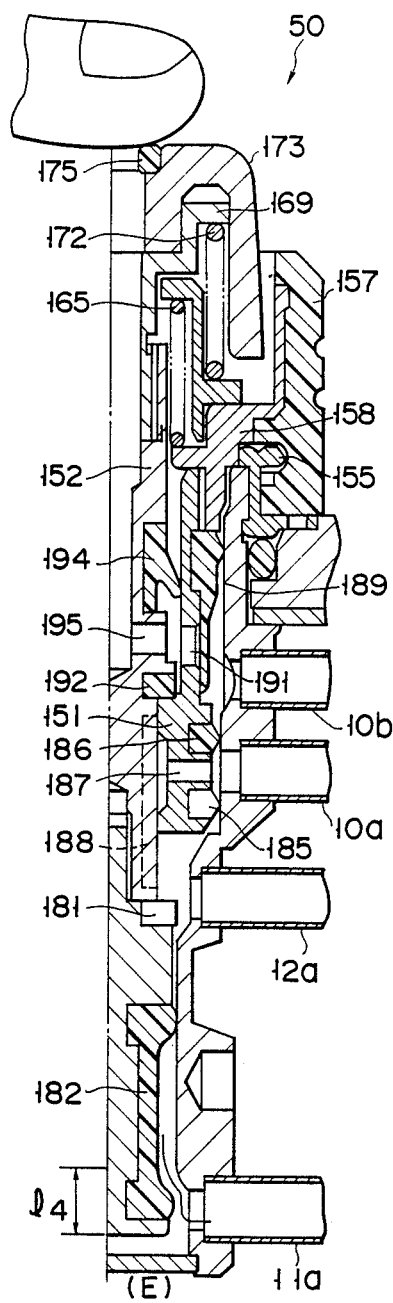

When water is to be supplied, second piston 152 is further pushed by l4 while closing opening 175 of leak hole 174, as shown by (E) in FIG. 17. Second compression spring 172 which is higher in spring force is also compressed together with first compression spring 165. When second piston 152 is pushed down like this from its first position where third flange 166 of spring receiving cylinder 162 is contacted with the face of stepped portion 167, sixth valve 192 is struck against the end face of stepped portion 193 of first piston 151 to thereby shut off grooves 188 and then leak hole 174 from lower side air supply tube 10b. No air is supplied accordingly. When air supply is stopped like this, the air flows into container 59 of water supply tank 14 through upper side air supply tube 10a, branch tube 32 and tube 60 and thus increases the pressure in container 59. As the result, water in container 59 flows into upper side water supply tube 11a through tube 61. As second valve 182 of second piston 152 is so lowered in this case as to communicate upper side water supply tube 11a with lower side tube 11b through its recessed portion 183, water which has reached the space in the bottom of valve seat 150 flows into lower side tube 11b through recessed portion 183, so that water can be supplied through nozzle 2a at operating section 2.

Gas can be supplied using switch valve means 50. Gas connector 35 is attached to gas supply base 17 at connector 13 of endoscope 1. Operating pipe 39 thus pushes piston 23 of air and gas switch valve 19 to thereby shield upper side air supply tube 10a and open upper side gas supply tube 12a. As the result, nonflammable gas can be supplied from gas bomb 20 through tube 37 and upper side gas supply tube 12a.

When switch valve means 50 is kept ready as shown by (C) in FIG. 16, the connecting end of upper side gas supply tube 12a is shielded by first and second valves 181 and 182 and no noninflammable gas is leaked outside.

When switch valve means 50 is under gas supplying condition as shown by (D) in FIG. 16, first valve 181 is separated from the lower end of first piston 151 and grooves 188 are opened. As described above in the air supply process, therefore, fifth valve 189 is lifted to allow gas to be fed into lower side air supply tube 10b which serves as the lower side gas supply tube. Noninflammable gas can be thus supplied into the cavity of the patient through nozzle 2a at inserted section 2. When gas is being supplied like this, it is not leaked outside through leak hole 174 and the like.

Container 59 of the water supply tank is pressurized by air supplied from the air supply pump through branch tube 32, as described above. Water is therefore kept ready to be supplied through upper side water supply tube 11a. When the operating button is pushed as shown by (E) in FIG. 17, therefore, water can be supplied as described above.

The switching of air and gas can be achieved only by attaching and detaching gas connector 35. This makes it easier and more convenient to use the endoscope. This also makes it possible to more easily confirm how the endoscope is used and prevent the endoscope from being mistakenly operated.

According to above-described switch valve means 50, air, water and gas can be supplied without replacing piston 151, 152 and the like. This eliminates troublesome parts exchange. The endoscope can be therefore used with more easiness and prevented from being mistakenly used for any purpose not intended. This guarantees safety.

The pressure in gas bomb 20 is set by the user and there is the possibility that the gas pressure is not certain. Even when first valve 181 is broken by high gas pressure or first piston 151 attached or detached, it is leak hole that is communicated. Therefore, no gas flows into lower side air supply tube 10b. Safety can be thus guaranteed. Further, even when first valve 181 is broken, the pressure in lower side air supply tube 10b is made higher due to the pressure in the cavity of the patient and the like than that in upper side gas supply tube 12a under the condition (C) shown in FIG. 16. Air and gas are not supplied accordingly.

Container 59 of water supply tank 14 can be pressurized by the gas pressure in gas bomb 20. It may be arranged in this case, for example, that pressure is adjusted through an orifice and the like on the line of gas tube 37.

Further, endoscope 1 may be of the fiber scope or electron scope type.

The second example of endoscope 1 can be used for both air and gas supply without exchanging valves. Therefore, it can be used with more easiness. In addition, the danger of mistakenly selecting wrong valves at the time of valve exchange can be eliminated, thereby enhancing safety extremely.

It should be understood that the present invention is not limited to the above-described embodiments but that various changes and modifications can be made without departing from the scope of claims appended hereto.

What is claimed is:

1. An endoscope including an elongated insertion section inserted into the cavity of a human body and provided with a nozzle at the foremost end thereof, an operating section connected to the other end of said insertion section and controlling it from outside the human body, and a universal code extending from said operating section, said endoscope further comprising
   a fluid source;
   a connector connected to that end of said universal code, opposite of said operating section, and also connected to said fluid source;
   a fluid supply tube means extending through said insertion section, operating section and universal code and communicating with said nozzle and also with said fluid source through said connector; and
   a switch valve means arranged within said fluid supply tube means, dividing said fluid supply tube means into upper and lower side tube means;
   wherein said switch valve means comprises a valve seat attached to said operating section and having an inner hole communicating with an inlet port means connected to said upper side tube means, and an outlet port means communicating with said lower side tube means, and a valve assembly means inserted into said inner hole of the valve seat, said valve assembly means being capable of moving between a first position where said inlet and outlet port means are shut off and a second position where they communicate with one another, said valve assembly means having a leak passage, which can be selectively closed, for allowing fluid to be released via the inlet port means to the outlet port means, and thereby released to the outside of said first position.

2. An endoscope according to claim 1, wherein said fluid source includes air and gas sources, said connector has a first base connected to said air source and a second base connected to said gas source and is provided with an air switch means therein, and said air switch means shields the upper side tube means from the first base when said gas source is connected to said second base and allows said upper side tube means to communicate with the first base when said gas source is detached.

3. An endoscope according to claim 2, wherein said valve assembly means has a first valve assembly for allowing the inlet port means to communicate with said leak passage when it is at said first position and shielding the inlet port means from said leak passage when it is at said second position, and a second valve assembly for allowing said outlet port means to communicate with said leak passage when it is at said first and second positions, and said first and second valve assemblies can be selectively inserted into said valve seat.

4. An endoscope according to claim 3, wherein said first valve assembly includes a check valve therein, said check value being capable of transporting a fluid flow from said inlet port means to said outlet port means therethrough when the outlet of the leak passage is closed.

5. An endoscope according to claim 4, wherein said upper side tube means has a first tube which communicates with said first and second bases, said lower side tube means has a second tube for enabling said gas or air source to communicate with said nozzle, said inlet port means has an air inlet port which communicates with said first tube, and said outlet port means has an air outlet port which communicates with said second tube.

6. An endoscope according to claim 5, wherein said fluid source includes a water source, said connector has a third base connected to said water source, said upper side tube means has a third tube which communicates with said third base, said lower side tube means has a fourth tube for enabling the water source to communicate with said nozzle, said inlet port means has a water inlet port which communicates with said third tube, and said outlet port means has a water outlet port that communicates with said fourth tube.

7. An endoscope according to claim 6, wherein said second valve assembly has a third position where it allows said air inlet port to communicate with said air outlet port, and allowing said water inlet port to communicate with said water outlet port.

8. An endoscope according to claim 7, wherein said water source includes a tightly-closed container in which water and air are contained, and said third base has a passage for enabling said water to communicate with said third tube and another passage for allowing said air to communicate with the first tube.

9. An endoscope according to claim 8, wherein said second valve assembly includes a check valve for enabling to flow from said air inlet port to said air outlet port when said second valve assembly is in said third position.

10. An endoscope according to claim 9, wherein said check valve has a lip seal, sealing said check valve with the circumferential face of said inner hole in said valve seat.

11. An endoscope according to claim 9, wherein said second valve assembly includes a first piston member for controlling the communication between said water inlet and said outlet ports, and a second piston member which is movable in said first piston member and controls the communication between said air inlet and outlet ports, and said outlet opening of said leak passage is formed in said second piston member at the outermost end thereof.

12. An endoscope according to claim 9, wherein said second valve assembly includes a first piston member for controlling the communication between said water inlet and outlet ports, and a second piston member movable along the circumferential portion of said first piston and controlling the communication between said air inlet and outlet ports, and said outlet opening of said leak passage is formed in said second piston member at the outermost end thereof.

13. An endoscope according to claim 12, wherein said first piston member of said second valve assembly is provided with axially-directed grooves for enabling said air inlet and said outlet ports to communicate with one another when said first piston member is in said third position.

14. An endoscope according to claim 2, wherein said fluid source includes a water source, said connector has a third base connected to said water source, said upper side tube means has a first tube which communicates with said first base, a fifth tube communicates with said second base, and a third tube communicates with said third base, said lower side tube means has a second tube for enabling said gas or air source to communicate with said nozzle and a fourth tube which enables said water source to communicate with said nozzle, said inlet port means has a gas inlet port of which communicates with said first tube and an air inlet port which communicates with said fifth tube, said outlet port means has an air outlet port which communicates with said second tube and a water outlet port that communicates with said fourth tube, and said valve assembly has a first position where said gas inlet port is shielded from said air outlet port, said air inlet port communicates with the atmosphere via said leak passage, and said water inlet port is shielded from said water outlet port, said valve assembly also has a second position where said air outlet port is shielded from said gas and air inlet ports and said water inlet and outlet ports communicate with one another, and further, said valve assembly has a third position where said air outlet port is shielded from said air and gas inlet ports.

15. An endoscope according to claim 14, wherein said valve assembly includes a check valve which enables air to flow from said air inlet port to said air outlet port when said leak passage is closed at said first position of said valve assembly.

16. An endoscope according to claim 15, wherein said valve assembly has a first piston member for controlling the communication between said water inlet and outlet ports, and a second piston member movable in the axial direction on the outer circumferential portion of said first piston member and controlling the communication between said air and gas inlet port and said air and gas outlet port.

17. An endoscope according to claim 2, wherein said operating section has a base member for housing said valve seat which is provided with a flange at that end thereof which is opposite to said operating section, and said valve assembly can be detachably adjoined to said base member via said flange.

18. An endoscope according to claim 14, wherein said operating section has a base member for housing said valve seat which is provided with a flange at that end thereof which is opposite to said operating section, and said valve assembly can be detachably joined to said base member by means of said flange.

19. An endoscope according to claim 16, wherein said valve assembly is urged to said first position.

20. An endoscope according to claim 19, wherein said valve assembly is urged to said first position.

* * * * *

UNITED STATES PATENT AND TRADEMARK OFFICE
CERTIFICATE OF CORRECTION

PATENT NO. : 4,800,869
DATED : JANUARY 31, 1989
INVENTOR(S) : SHIGERU NAKAJIMA

It is certified that error appears in the above-identified patent and that said Letters Patent is hereby corrected as shown below:

Title page:

Item [30], third priority serial number "62-31937" should read -- 62-319378 --

Signed and Sealed this

Sixth Day of February, 1990

*Attest:*

JEFFREY M. SAMUELS

*Attesting Officer*     *Acting Commissioner of Patents and Trademarks*